Figure 1:
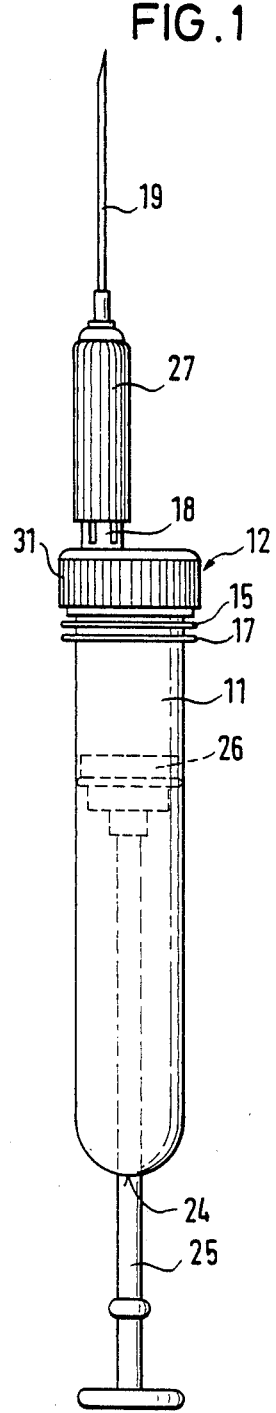

United States Patent [19]

Vollmar

[11] Patent Number: 4,940,154
[45] Date of Patent: Jul. 10, 1990

[54] LIQUID STORAGE CONTAINER WITH CLOSURE CAP

[75] Inventor: Herbert Vollmar, Much, Fed. Rep. of Germany

[73] Assignee: Walter Sarstedt Geraete und Verbrauchsmaterial fuer Medizin & Wissenschaft, Nuembrecht-Rommelsdorf, Fed. Rep. of Germany

[21] Appl. No.: 363,669

[22] Filed: May 26, 1989

[30] Foreign Application Priority Data

May 27, 1988 [DE] Fed. Rep. of Germany ....... 3818115

[51] Int. Cl.$^5$ .......................................... B65D 41/46
[52] U.S. Cl. ...................................... 215/249; 215/252
[58] Field of Search ................ 215/249, 251, 252; 53/490, 485, 449

[56] References Cited

U.S. PATENT DOCUMENTS

| | | | |
|---|---|---|---|
| 3,480,172 | 11/1969 | Shine | 215/251 |
| 3,871,545 | 3/1975 | Bereziat | 215/249 |
| 4,378,812 | 4/1983 | Sarstedt | 128/765 |
| 4,394,918 | 7/1983 | Grussen | 215/252 X |
| 4,592,475 | 6/1986 | Hannon | 215/252 |

FOREIGN PATENT DOCUMENTS 2356007 5/1974 Fed. Rep. of Germany ...... 215/252

Primary Examiner—Donald F. Norton
Attorney, Agent, or Firm—Townsend & Townsend

[57] ABSTRACT

A liquid storage container has a tubule (11) which is open at one end and which is closed in liquid-tight manner at the front end face by a closure (12) which can be removed and/or opened for the filling of liquid into the tubule and/or for the removal thereof. An auxiliary closure cap (14) is provided for the closed tubule and has a locking ring 13 at its front open side. The auxiliary closure cap (14) is mountable onto the front end of the tubule (11), so that it covers over the closure (12) towards the outside. The locking ring (13) then snaps over a latch means (15) provided at the outer wall of the tubule (11) in its front region. The locking ring (13) is contrived so that it cannot be straightforwardly removed from the latch means by pulling it axially in the forward direction. In this way it is possible to check whether the liquid storage container has been tampered with.

12 Claims, 4 Drawing Sheets

LIQUID STORAGE CONTAINER WITH CLOSURE CAP

The invention relates to a liquid storage container, in particular for body fluids and/or for the transport of liquids from a filling location to an investigation location, the container comprising a preferably cylindrical tubule open at one end and closed in liquid-tight manner at the front end face by a closure which is removable and/or openable for the filling of the container with a liquid and/or for the removal of liquid.

Such liquid storage containers are for example used for the transport to an investigating laboratory of body fluids extracted from a patient by a doctor or a nurse. The body fluid filled into the tubule can be urine, saliva or blood. In general such liquid storage containers have a removable closure at their open end whereas they are closed in liquid-tight manner at the other end. The liquid can be filled into the tubule by opening the closure at the front end whereupon the closure is then set in place and the tubule is sent to a laboratory where the closure is removed and the liquid is passed on for further investigation, either before or after initial processing, for example in a centrifuge.

A problem with such liquid storage containers lies in the fact that any form of manipulation should be avoided in the sense that, after closing of the tubule filled with the liquid by the authorised person and prior to arrival of the liquid storage container in the laboratory, any renewed opening of the container should be prevented, or should at least take place in such a way that it can be recognised on arrival of the tubule in the laboratory. This is intended to prevent an authorised person either substituting the liquid contained in the tubule for a different liquid or additionally adding some form of other substances into the tubule. Such manipulations must for example be feared when the tubule contains a blood sample taken from a driver which is to be investigated in the laboratory for its alcohol content.

The object of the invention is thus to provide a liquid storage container of the initially named kind which cannot be unrecognisably manipulated by unauthorised persons after filling with a liquid and mounting of the closure in such a way that the content of the container can be falsified. Moreover, any unauthorised opening which may nevertheless be effected should be capable of being straightforwardly recognised at the destination.

In order to satisfy this object the present invention provides a liquid storage container of the initially named kind which is characterised in that a closure cap is provided and has at its open end a locking ring which can be torn away, with the closure cap being mountable onto the front end of the tubule and covering over the closure towards the outside in such a way that the locking ring snaps over a latch means provided at the outer wall of the tubule, preferably in its front region, with the locking ring not being straightforwardly removable from the latch means by pulling it axially in the forward direction.

The concept underlying the invention is thus to be seen in the fact that the authorised person who filled the tubule with liquid and mounted the closure can push the closure cap of the invention into place by hand, i.e. without a tool, onto the front end of the closed tubule. In so doing the locking ring snaps onto the latch means provided on the tubule in such a way that removal of the closure cap is not possible without destroying the tearable connection between the locking ring and the closure cap. In this way persons who wish to open the container without authorisation are warned against doing it because they are not able to reclose the broken tearable connection between the closure cap and the locking ring. Should therefore an unauthorised person nevertheless tear off the closure cap or separate it from the locking ring then this will be recognised at the destination, for example in the investigating laboratory, and the liquid contained in the tubule can be thrown away as being unsuitable for the investigation. The possibility then exists of immediately acquiring a new liquid sample from the sender.

Such "originality closures" are omittedly known per se for the most diverse types of liquid containers; they are however already applied by the manufacturer by means of suitable machines and tools and during manufacture of the closure so that filling of the container outside of the fractory is not possible. The basic concept of the present invention consists however, in contrast, in delivering the closure cap having the tearable locking ring to the user in a state separate from the liquid storage container. The user is then able to first apply the closure cap by hand and without a special tool in order to seal the container after using the liquid container, i.e. after filling it with the intended liquid. The closure for the tubule which is already present is thus secured against an authorised opening by the additionally applied closure cap. The desired break positions must be adequately stable for the handling and setting in place of the closure cap.

The ring projection can, when manufacturing a tubule in plastic, be molded on in one piece. The ring projection is preferably coaxial to the right-cylindrical tubule and has a uniform width and thickness.

The construction of the locking ring so that it carries latch projections at the radially inner side and distributed around the periphery, with the latch projections entering into latching engagement with the latch means, means that the locking ring can be snapped into place without substantial effort. At the same time a considerable resistance is created against axial withdrawal of the closure cap so that on pulling axially on the closure cap the locking ring does not release from the latch means, but instead the auxiliary closure cap fractures at the desired break locations between the body of the closure cap and the locking ring.

The auxiliary closure of the invention is used to particular advantage with a liquid storage container having a closure in the form of a screw cap which engages around the front end of the tubule. Such liquid receiving containers are frequently used for blood extraction (DE-PS No. 29 48 653).

In order that the invention can be used with a liquid receiving container of this kind, in particular a liquid receiving container suitable for the taking of blood, a construction is preferably provided which is characterised in that the locking ring is arranged directly behind the screwed on screw cap and projects radially outward approximately to the level of the outer diameter of the screw cap. The locking or the latch projections should slide frictionally over the outer wall of the screw cap but should not jam on it when the auxiliary closure cap is pushed into place over the screw cap.

In other words the auxiliary closure cap which is set in place should completely close off the screw cap from the outside, so that the screw cap cannot be removed without pulling off the closure cap, i.e. without separating the closure cap from the locking ring. On the other hand, this embodiment results in an effortless separation of the closure cap from the locking ring since on rotating the screw cap by means of the closure cap which is pushed onto it the latter is axially separated from the locking ring which is in turn retained by the latch means on the tubule. In this way the desired break locations between the closure cap and the locking ring can be effortlessly destroyed. For this purpose provision should expediently be made that the closure cap tapers above the screw cap or has suitable abutments there in such a way that on undoing the screw cap the closure cap is moved forwardly with the screw cap.

A particularly advantageous embodiment is characterised in that a cover ring is provided at the outer wall of the tubule at a distance behind the latch means, with the cover ring covering over the locking ring and the latch means from the outside and preventing manipulation when the closure cap is set in place and the locking ring is not torn away. In this way manipulation of the closure using tools at the locking ring or at the latch means is prevented, since the cover ring prevents the tools acting on the latch means. Should the cover ring be destroyed by means of tools then this can be recognised in the laboratory in just the same way as the separation of the closure cap from the locking ring.

The invention can also be used to particular advantage with liquid receiving containers having a preferably cylindrical projection which projects forwardly from the closure and has an axial through-passage, with a closure member which can be penetrated by the rear end of a cannula sharpened at both ends being arranged in the projection (DE-PS No. 29 48 653). In this case the closure cap could have a cap projection at its inner side, with the cap projection covering over the front end of the projection and preferably sealingly closing it when the closure cap is set in place.

The screw cap which is applied to the tubule generally has a surface profile comprising axial ribs. In this case the invention provides, that a rotationally fixed connection is present between the mounted closure cap and the screw cap which permits the screw cap to be unscrewed by rotating the closure cap. The closure cap thus additionally serves as a tool for the actuation of the screw cap.

A construction in which the cover ring has a somewhat larger outer diameter than the inner diameter of the locking ring, and an axial spacing from the latch means such that the mounted locking ring cannot be straightforwardly pushed radially over the cover ring ensures that the locking ring which remains on tearing off the closure cap is retained between the latch means and the cover ring. In this way it is possible to recognise at once at the destination, even when the closure cap is not refitted, that a closure cap had been mounted on the front end of the container but had however been torn away during the transport.

Figure 2:
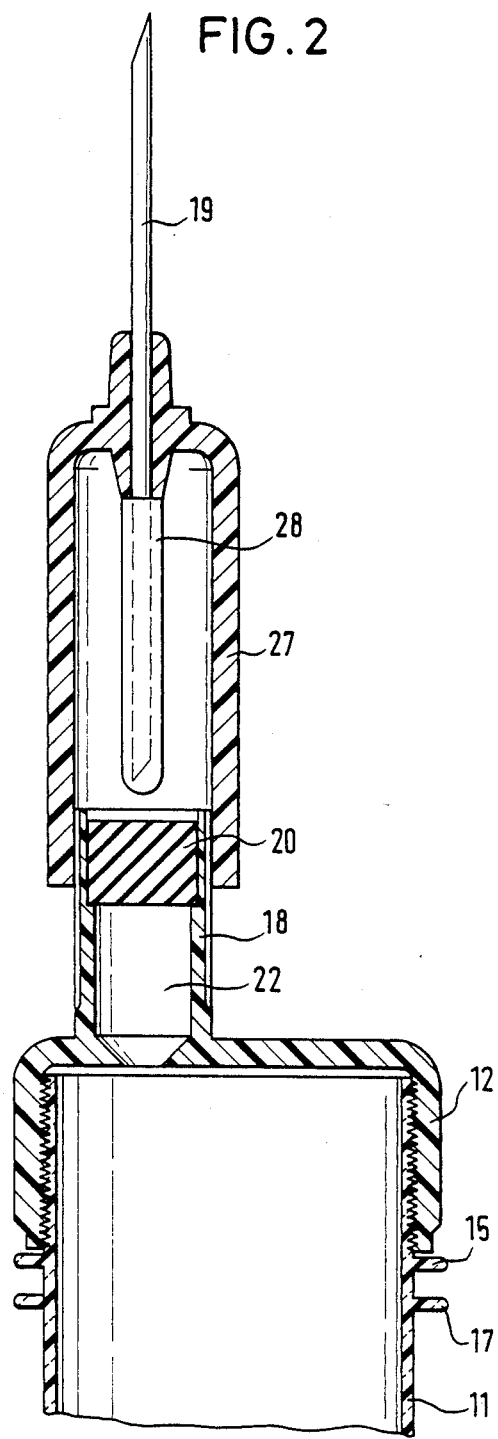
Figure 3:
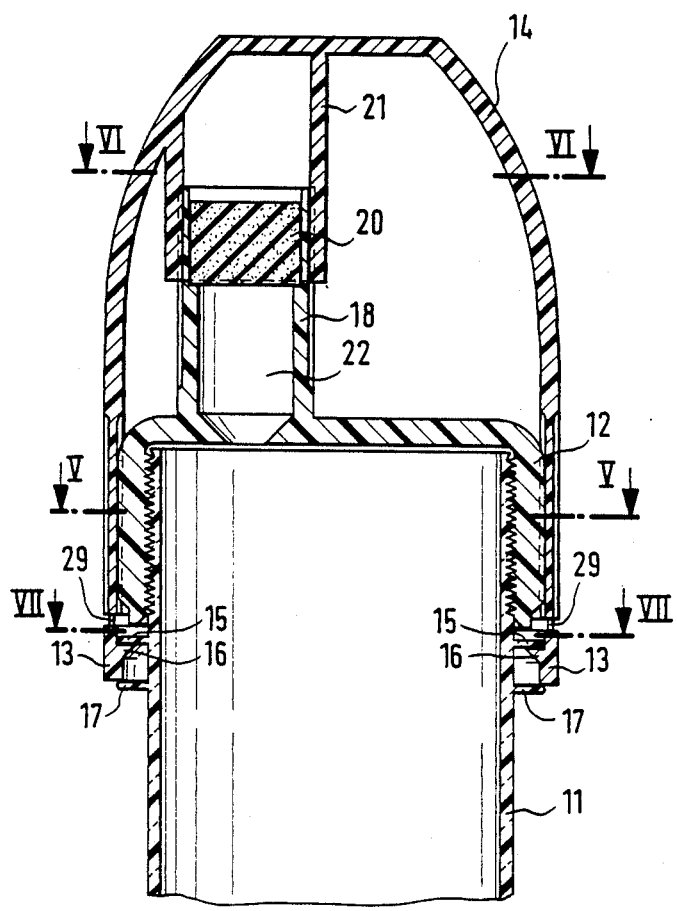
Figure 4:
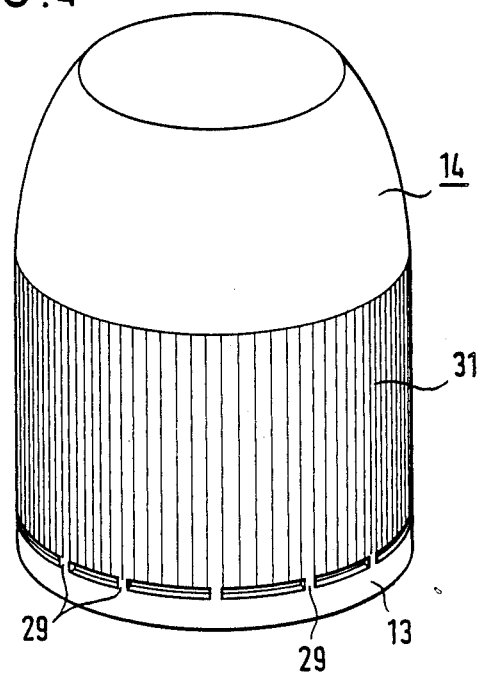
Figure 5:
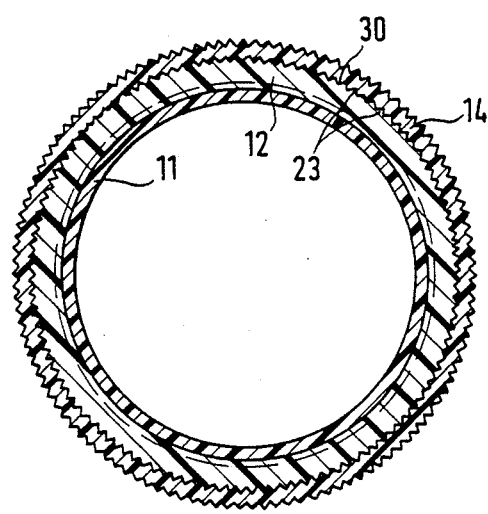
Figure 6:
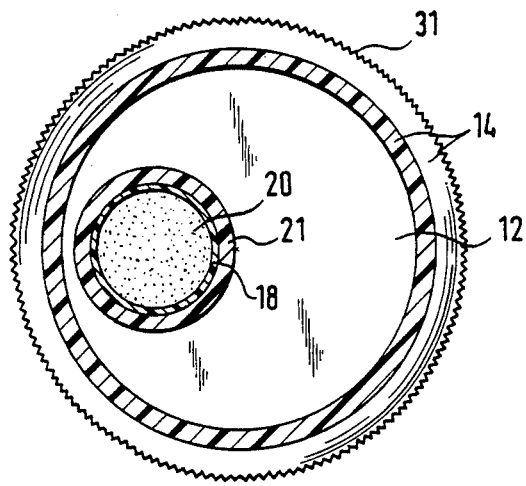
Figure 7:
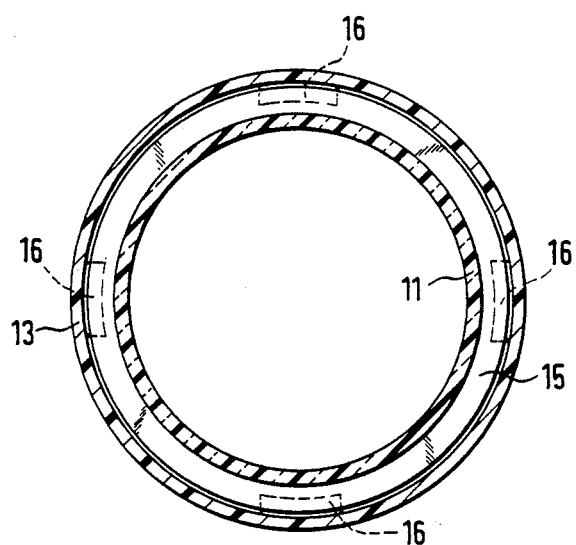

The invention will be described in the following by way of example and with reference to the drawings in which are shown:

FIG. 1 a schematic sideview of a liquid storage container in accordance with the invention in the form of a blood sampling device in the position of use without a closure cap mounted thereon, FIG. 2 an enlarged sectional view of the front part of the liquid storage container of FIG. 1, FIG. 3 a sectional view analogous to FIG. 2, however with the guide sleeve with the cannula being removed and in its place a closure cap with a locking ring in accordance with the invention being mounted on the front end of the tubule, FIG. 4 a schematic perspective view of the closure cap of the invention with locking ring, FIG. 5 a schematic section in accordance with the line V—V in FIG. 3, FIG. 6 a section on the line VI—VI in FIG. 3, and FIG. 7 a section in accordance with the line VII—VII in FIG. 3.

In all figures of the drawings the same reference numerals are used to designate parts which correspond with one another.

As seen in FIGS. 1 and 2 a piston rod 25 slidingly passes through an opening in the rounded rear end 24 of a right-cylindrical tubule of plastic. At its front end the piston rod 25 carries a piston 26 which is axially slidably disposed in the interior of the tubule 11. A screw cap 12 is screwed onto the front end of the tubule 11 which is provided with an outer thread. The screw cap 12 has an axially forwardly projecting right-cylindrical projection 18 in which an axial passage 22 is provided, with the passage in turn being closed at is front end by an elastic closure member 20.

A guide sleeve 27 is pushed from the front end onto the projection 18 and has a cylindrical inner surface complementary to the projection 18. The guide sleeve 27 is open at its rear end and closed at the front end. A cannula 19 which is sharpened at both ends is secured to the guide sleeve and passes through the front end thereof. The rear end of the cannula 19 is covered over by a resilient hose 28.

If the guide sleeve 27 is pushed from the position of FIG. 2 further onto the projection 18 then the rear end of the cannula 19 first punctures the elastic hose 28 and then the closure plug 20 which it finally fully penetrates, so that it opens into the through passage 22. During this the hose 28 is pushed together in the manner of a concertina. Blood can now be taken from the vein of a patient with the illustrated arrangement by pushing the cannula 19 into the vein. During this extraction of blood the piston 26 is retracted.

As so far described the liquid receiving container which serves for the extraction of blood is known from DE-PS No. 29 48 653.

In accordance with the invention a one-piece ring projection 15 is provided in accordance with FIG. 2 on the outer wall of the tubule 11 directly behind the screw cap 12 which is screwed thereto, with the ring projection 15 being coaxial to the tubule 11. A cover ring 17 which is likewise coaxial to the tubule 11 is located at a small distance behind the ring projection 15.

After the taking of blood the guide sleeve 27 is drawn off to the front whereupon an auxiliary closure cap 14, which has a locking ring 13 arranged at its open end via desired break locations 29, is pushed, in accordance with FIG. 3, from the front onto the tubule 11 with the screw cap 12 still filled. The locking ring 13 has, in accordance with FIGS. 3 and 7, four latch projections 16 which are distributed around the periphery and which are angled at the rear so that they run up onto the ring projection 15 but are in contrast flat at the front so that after they have snapped onto the ring projection 15 they can no longer axially be drawn away forwardly over the ring projection 15.

The inner circumference of the locking ring 13 is so formed that it fits from the front axially over the ring projection 15 so that the sloping rear surfaces of the latch projections 16 can slide up onto the ring projection 15 with resilient dilation of the locking ring 13 and can finally snap behind the ring projection 15.

The inner diameter of the rear end of the closure cap corresponds to the outer diameter of the screw cap 12 so that the rear part of the closure cap 14 contacts the outer circumference of the screw cap 12 in form-locked manner, with the screw cap 12 being provided at the outside with ribbing consisting of axial ribs 23. At the inside the closure cap 14 is provided with a complementary surface profile 30 so that, when the closure cap 14 is mounted in accordance with FIG. 3, a rotationally fixed, form-locked connection is present between the closure cap 14 and the screw cap 12. The closure cap 14 preferably tapers above the screw cap 12 in such a way that substantial further axial sliding of the closure cap 14 onto the screw cap 12 beyond that shown in FIG. 3 is not possible.

The rear edge of the closure cap 14 preferably closes approximately flush with the rear edge of the screw cap 12. The locking ring 13 is located directly behind the screw cap 12. The axial extent of the locking ring 13 in accordance with FIG. 3 is such that it extends when the closure cap 14 is mounted only approximately up to the cover ring 17. The outer diameter of the cover ring 17 is fractionally larger than the inner diameter of the locking ring 13 at the rear end, so that after the snapping of the locking ring onto the ring projection 15 illustrated in FIG. 3 further axial displacement of the locking ring 13 and thus of the closure cap 14 to the rear is not possible. In this manner the position of the closure cap 14 on the tubule 11 is uniquely defined.

At the front inner side the closure cap 14 has, in accordance with FIGS. 3 and 6, a cap projection 21 which extends axially rearwardly from the front wall, with the cap projection being molded in one piece with the closure cap 14, which preferably consists of plastic. The cap projection 21 extends coaxially to the projection 18. When the closure cap 14 is set in place the hollow cap projection 21, which is preferably hollowed out in the manner of a right cylinder, is mounted axially on the projection 18 in the manner which can be seen from FIGS. 3 and 6 and closes the latter against the uncontrolled running out of blood, which could be present at the front surface of the elastic closure member 20.

In accordance with the invention the closure cap is also provided with ribbing 31 at its outer periphery as is indicated in FIGS. 4 and 6.

The manner of operation of the liquid receiving container is as follows:

After the extraction of blood the guide sleeve 27 (FIG. 2) is pulled off and is either left in the vein of the patient or disposed of.

The closure cap which can be seen from FIG. 4 is then pushed from the front in accordance with FIG. 3 onto the front end of the liquid container which has been exposed by the removal of the guide sleeve 27. The latch projections 16 slide on the outer periphery of the screw cap 12, with slight resilient dilation of the rear cylindrical part of the closure cap 14, until they finally snap behind the ring projection 15. During this the cap projection 21 is sealingly mounted onto the projection 18 or at least in a manner which prevents the uncontrolled running out blood. The liquid receiving container can now be despatched in the position shown in FIG. 3.

In the laboratory, where the content of the tubule 11 is to be investigated, the screw cap 12 is unscrewed by grasping the closure cap 14 with two fingers at the level of the screw cap 12 and rotating it in the counter-clockwise sense. During this the torque exerted on the closure cap 14 is transferred to the screw cap 12 and the latter is axially removed from the tubule 12. As the latch projections 16 engage axially non-releasably behind the ring projection 15 the desired break points 29 fracture during the unscrewing process and the closure cap 14 is separated from the latch ring 13 which, as a result of the described construction arrangement remains held between the ring projection 15 and the cover ring 17.

After the removal of the closure cap 14 with the screw cap 12 the content of the tubule 11 can be extracted.

Should the screw cap 12 have been removed and remounted in the meantime then one can readily recognise this from the fracturing of the desired break locations 29 which has taken place.

Removal of the closure cap 14 is also not possible by inserting a tool behind the locking ring 13 since this is prevented by the cover ring 17 formed in one piece with the tubule 11.

In accordance with the invention the cap projection 21 can also be so formed that it can be sealingly mounted onto a customary cannula at the front end of the screw cap 12. In this arrangement the cap projection 21 should be made complementary in shape to the outer shape of the cannula projection.

I claim:

1. A liquid storage container for transporting liquids from a filling location to an investigation location, the container comprising:
   a tubule having an open front end and an outer wall having a latching means adjacent to the front end;
   a removable closure for the front end for filling and emptying the tubule;
   a closure cap mountable on the front end of the tubule for covering the closure, the closure cap having an opening adapted to receive the closure therein and including a locking ring attached to the closure cap defining a tearable connection, the locking ring engaging the latching means on the tubule when the closure cap is mounted on the front end of the tubule for preventing the removal of the closure cap unless the tearable connection is first destroyed.

2. A container according to claim 1, wherein the tubule is cylindrical.

3. A container according to claim 1, wherein the latching means is a ring projection around the outer wall of the tubule and is molded in one piece with the tubule.

4. A container according to claim 1, wherein the locking ring includes a plurality of latch projections projecting radially inward, the latch projections entering into a latching engagement with the latching means when the closure cap is mounted on the front end of the tubule.

5. A container according to claim 1, wherein the closure is a screw cap having an outer diameter and the locking ring is arranged directly behind the screw cap when the closure cap and screw cap are mounted on the front end of the tubule, the locking ring projecting radially outward approximately to the level of the outer diameter of the screw cap.

6. A container according to claim 5, wherein the locking ring and the latch projections slide with friction over the screw cap as the closure cap is mounted on the front end of the tubule.

7. A container according to claim 5, wherein the screw cap includes an outer periphery having a first surface profile and the closure cap includes an inner periphery having a diameter corresponding to the outer diameter of the screw cap, the inner periphery further having a second surface profile complementary to the first surface profile such that when the closure cap and screw cap are mounted on the front end of the tubule, the closure cap is connected to the screw cap in a rotationally fixed manner that allows force to be transmitted from the closure cap to the screw cap.

8. A container according to claim 7, wherein the closure cap is connected to the screw cap in a form-locked manner.

9. A container according to claim 1, wherein the outer wall of the tubule further comprises a cover ring behind the latching means, the cover ring preventing manipulation of the locking ring when the closure cap is mounted on the front end of the tubule.

10. A container according to claim 9, wherein the cover ring has a diameter and the locking ring has an inner diameter, the diameter of the cover ring being slightly larger than the inner diameter of the locking ring, and wherein the cover ring is positioned on the outer wall of the tubule such that the locking ring cannot be radially displaced over the cover ring when the closure cover is mounted on the front end of the tubule.

11. A container according to claim 1, wherein the closure includes a cylindrical projection which projects forwardly from the closure, the clyindrical projection having an axial through-passage and a closure member, and the closure cap includes an inner side having a cap projection, the cap projection being positioned such that the cap projection covers over and seals the cylindrical projection when the closure cap is mounted on the front end of the tubule.

12. A method of securing a liquid storage container against unauthorized opening comprising the steps of:
  selecting a tubule having an open front end and a latching means adjacent to the front end;
  placing a removable closure on the front end;
  placing a closure cap over the closure, the closure cap having an opening adapted to receive the closure therein and including a locking ring attached to the closure cap by a tearable connection, the locking ring engaging the latching means on the tubule when the closure cap is mounted on the front end of the tubule, thereby preventing removal of the closure cap without destroying the tearable connection.

* * * * *